United States Patent [19]

Hauser

[11] Patent Number: 5,102,389
[45] Date of Patent: Apr. 7, 1992

[54] MEMBRANE COMPOSITE

[75] Inventor: Jean-Luc Hauser, Antibes, France

[73] Assignee: Cordis Corporation, Miami Lakes, Fla.

[21] Appl. No.: 497,260

[22] Filed: Mar. 22, 1990

[30] Foreign Application Priority Data

Mar. 28, 1989 [FR] France .................. 89 03998

[51] Int. Cl.⁵ .......................................... A61M 11/00
[52] U.S. Cl. ...................... 604/93; 604/131; 604/153; 604/891.1; 128/DIG. 12
[58] Field of Search .............. 604/93, 181, 185, 891.1, 604/153, 131, 132; 128/DIG. 12

[56] References Cited

U.S. PATENT DOCUMENTS

| | | | |
|---|---|---|---|
| 3,922,468 | 11/1975 | Burke, Jr. et al. | 428/414 |
| 4,548,605 | 10/1985 | Iwamoto et al. | 604/410 |
| 4,668,231 | 5/1987 | de Vries et al. | 604/891.1 |
| 4,718,894 | 1/1988 | Lazorthes | 604/93 |
| 4,738,657 | 4/1988 | Hancock et al. | 604/93 |
| 4,772,263 | 9/1988 | Dorman et al. | 604/891.1 |
| 4,840,615 | 6/1989 | Hancock et al. | 604/93 |
| 4,898,585 | 2/1990 | Borsanyi et al. | 604/153 |
| 4,902,278 | 2/1990 | Maget et al. | 604/891.1 |
| 4,904,241 | 2/1990 | Bark | 604/93 |

FOREIGN PATENT DOCUMENTS

| | | |
|---|---|---|
| 260081 | 3/1988 | European Pat. Off. . |
| 2855694 | 3/1990 | Fed. Rep. of Germany . |
| 2125127 | 9/1972 | France . |

Primary Examiner—Gene Mancene
Assistant Examiner—Michael Lynch
Attorney, Agent, or Firm—Gerstman & Ellis, Ltd.

[57] ABSTRACT

The invention relates to a membrane intended to form the external wall of a reservoir which is capable of being implanted under the skin of a patient. It comprises at least one layer (3) of a fibrous material arranged between two layers of a biocompatible elastomer.

20 Claims, 1 Drawing Sheet

MEMBRANE COMPOSITE

BACKGROUND OF THE INVENTION

The present invention relates to a membrane intended to close and form part of the external wall of a reservoir which is capable of being implanted under the skin of a patient. The membrane may also be used elsewhere as desired, wherever strength and flexibility are needed.

Such reservoirs are well-known, for example see French Patent Publication No. 2,582,222, corresponding to U.S. Pat. No. 4,718,894. These reservoirs are generally made of a hollow, rigid body closed by one or two membranes defining, with the body, a chamber of variable volume.

At least one other membrane or other barrier, typically of smaller size than the closure membrane, is generally mounted on the body in addition to the preceding membrane or membranes, to provide an injection site for filling the reservoir.

Also, a pump with manual, electronic, or electromechanical control allows a dose of the liquid contained in the reservoir to be transferred to a catheter which terminates at a predetermined site in the body of the patient.

When the assembly has been implanted under the skin of the patient, with the closure and filling membranes on the exterior side, the reservoir may be regularly filled using an injection syringe, the needle of which is successively caused to pass through the patient's skin and the membrane of the injection site.

Once the reservoir is filled, the patient can then himself deliver the medicament contained in the reservoir to the chosen site, with the aid of the pump.

It is, however, essential that the person carrying out the filling of the reservoir penetrates the injection site membrane, and not a closure membrane of the reservoir or a pump control.

The present invention aims to provide a membrane which is not perforable by a hypodermic needle, and nevertheless retains all the characteristics required of such a membrane, for example its flexibility, allowing variation in the volume of the chamber. Also, the membrane of this invention can prevent diffusion of substances of low molecular weight, and exhibits good biocompatibility.

DESCRIPTION OF THE INVENTION

For this purpose, the membrane according to this invention is characterized by the fact that it comprises at least one layer of a fibrous material arranged between two layers of a biocompatible elastomer.

The fibrous material may comprise polyaramide fibers such as those sold under the brand Kevlar by the Dupont de Nemours company, or alternatively, carbon, metal, or other fibers.

The density and the orientation of the fibre network must be such that a needle cannot cross it with normal pressures. The thickness of the fibers must also be such that they can resist the pressure which may be imposed by the point of a needle. These fibers can be presented in one or several distinct layers, as desired.

The biocompatible elastomer layers can, for example, each comprise a layer of silicone or polyurethane.

Such a reinforced membrane then cannot be accidentally perforated, but nevertheless it retains the flexibility necessary for the variation of the reservoir volume. This membrane also allows the maximum capacity of the reservoir to be increased without risk, since it is of great strength and is thus exceedingly unlikely to rupture.

The fibrous material is preferably woven, and stabilized in a layer of resin to bind crossing fibers together. The regularity of the fibre network is thus assured. In addition, the resin prevents the fibers of the network from moving apart to allow the passage of a needle.

The resin can be any suitable type, for example an epoxy resin or a polyamide resin.

Advantageously, provision is made, in addition, to provide a water-excluding film between the layer of fibrous material and one of the biocompatible elastomer layers. This film is to give the membrane a good ability to exclude substances of low molecular weight such as water vapor. Among others, polyethylene, polyaramide, polyamide or polyester films may be used for this purpose. Biaxially oriented polyester films, for example those sold under the brand Mylar by the Dupont de Nemours Company, are currently preferred.

In order to allow better adhesion between the water-excluding film and the resin which stabilizes the fibrous material, another elastomer layer can be provided between the resin and the water-excluding film. A bonding primer may optionally be used to improve the adhesion.

A particular method of implementation of the invention will now be described as a non-limiting example, with reference to the drawings attached.

DESCRIPTION OF SPECIFIC EMBODIMENTS

Figure 1:
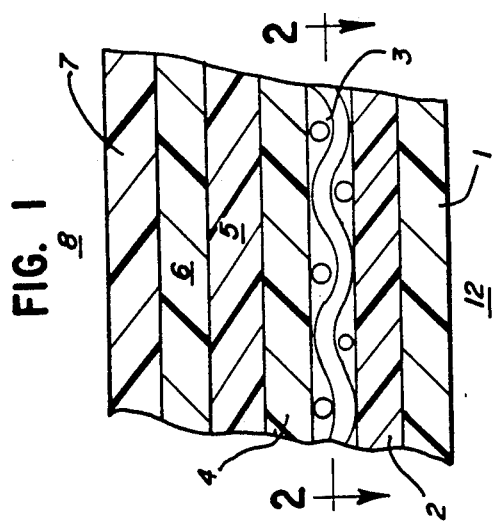
FIG. 1 is a schematic view of a membrane according to the invention in transverse section.

The membrane 11a, 11b represented in the drawings is a multilayer composite comprising, successively from the exterior 12 to the interior 8 of the reservoir 14, a layer of biocompatible silicone 1, a layer of epoxy resin 2, a cloth 3 of one or more layers of woven Kevlar fibers 16, a second layer 4 of epoxy resin, an optional intermediate flexible adhesive silicone layer 5, Mylar plastic film 6, and a third layer of biocompatible silicone 7. Layers 1, 5 and 7 are preferably elastomers, and may be polyurethane or the like as a substitute for silicone, if desired.

Layer 1 ensures biocompatibility with respect to the body of the patient, while layer 7 ensures biocompatibility with respect to the product contained in the interior 8 of the implanted reservoir 14.

The resin layers 2 and 4 are bonded to cloth 3, to ensure its stability, preventing its filaments 16 from moving apart. For example, an epoxide or polyimide resin is preferred for use as the filament stabilization resin in layers 2 and 4.

It would also be possible, instead of using two layers 2 and 4 and the cloth 3, to use a pre-impregnated cloth directly, in which filaments 16 are bonded together by a resin primer (such as epoxy) at their crossing points. This type of fabric has the advantage of being capable of being pre-formed and then directly injection-moulded with silicone layer 1. Such a pre-impregnated cloth is sold, for example, by the French company Brochier.

The intermediate silicone elastomer layer 5 allows bonding with the Mylar film 6 to be ensured, restricting or preventing diffusion of substances contained in the reservoir 8 through membrane 11a, 11b.

As an example, the Kevlar cloth 3 used can be a satin, woven with filaments 16 of the order of 0.3 mm. in diameter, the distance between filaments being on the order of 0.1 mm., to prevent perforation of the membrane by a standard needle.

The silicone layers 1, 5 and 7 can have a thickness on the order of 0.5 mm., and the whole of the epoxy layers 2 and 4, and the cloth 3, can together have a thickness on the order of 0.5 mm..

The applicant has thus constructed a membrane giving satisfactory results by cold-forming of a Kevlar cloth, optionally pre-impregnated with epoxy resin, and curing and after-baking this pre-impregnated cloth.

Silicone elastomer layers 2, 5 may then each be moulded onto one side of the epoxy impregnated fabric 2, 3, 4 using an injection press, at 300 bars and 150° C.

Thin Mylar plastic film 6 may be glued to the other side, after adding optional layer 5, when used, after which another moulding or extrusion 7 of silicone elastomer may be carried out to cover the Mylar plastic film 6.

Figure 2:
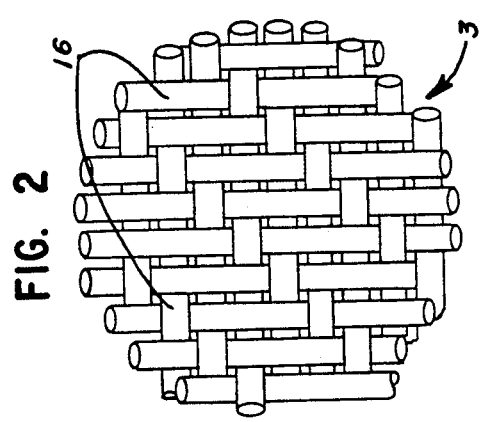
FIG. 2 is a greatly enlarged view of FIG. 1, taken in section along line II—II of FIG. 1.
Figure 4:
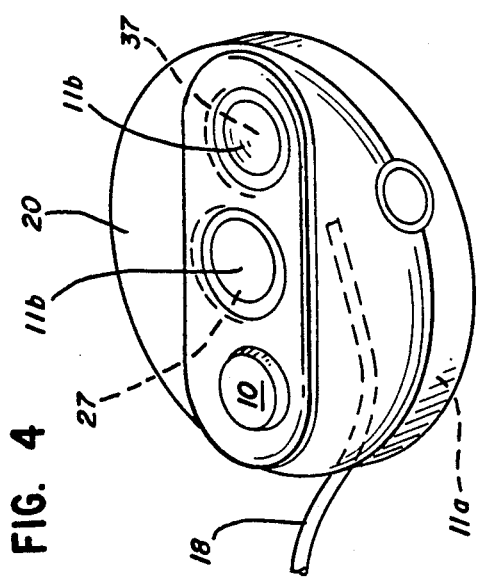
FIG. 4 is a perspective view of the implantable pump and reservoir of FIG. 3.
Figure 3:
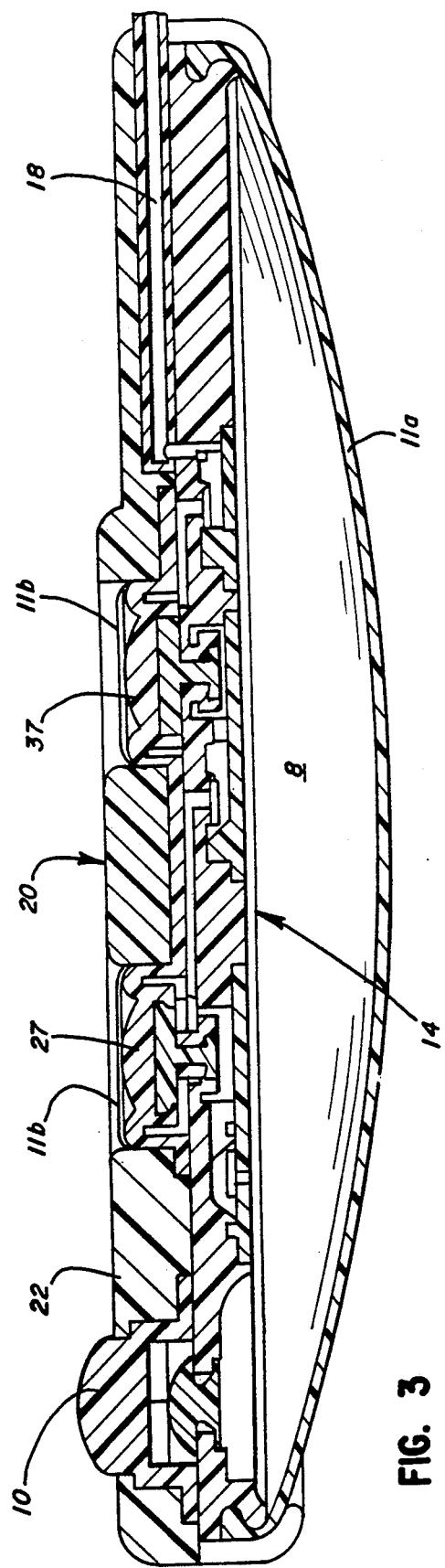
FIG. 3 is a sectional view of an implantable pump and reservoir using the membrane of FIGS. 1 and 2.

Referring particularly to FIGS. 3 and 4, an implantable, hand-operable dispenser for fluid medicaments is disclosed, which dispenser defines a reservoir portion 14 in which the interior 8 thereof is partially defined by membrane 11a as shown in FIGS. 1 and 2 and described above. Membrane 11a is tough and resistant to a needle puncture or other rough handling.

The specific design of implantable dispenser which is disclosed here is described in detail in De Vries et al. U.S. Pat. No 4,668,231, issued May 26, 1987, the disclosure of which is incorporated by reference herein. The dispenser which is shown in FIGS. 3 and 4 may be made in accordance with the teachings of that cited patent, subject to the modifications as described herein.

As taught in the previously described patent, the dispenser describes not only a reservoir portion 14, but also a fluid dispensing portion 20, the two portions being connected together and coacting with each other. Fluid dispensing portion includes a pair of resilient pads 27, 37 which, after implantation of the dispenser in the human body, may be manually manipulated by pressing the overlying skin of the body with the fingers, to cause dispensing of a metered amount of fluid from reservoir interior 8 through tube 18 when the respective pads 27, 37 are pressed in proper order, as described in the cited patent.

In accordance with this invention, additional pieces of the membrane 11b of this invention may be attached to the respective pads 27, 37 to prevent hypodermic needle penetration from outside the skin through the pads 27, 37, because the membrane of this invention, as previously described, can be impervious to hypodermic needle penetration.

Domed pad 10, as shown in FIGS. 3 and 4, may serve as a supply port, being penetrable by a hypodermic needle passing through the skin and then through the domed pad 10, to provide resupply medicament to the interior of reservoir 8. Since no membrane 11 covers domed pad 10, it is penetrable by a hypodermic needle. Thus, it is not possible to damage the dispensing device by an erroneous attempt to inject resupply medicament with the needle wrongly placed. If the needle is not placed to penetrate the skin and then domed pad 10, it cannot penetrate the dispensing device at all. Housing portion 22 may be made of a hard plastic which is also resistant to needle penetration.

Hence, the dispensing device may be safely and conveniently operated, while the flexible membranes 11a and 11b used in the device protect against needle puncture, while being flexible to permit the manipulation of pads 27, 37, and the necessary expansion and contraction of reservoir interior 8, as the volume of fluid therein is increased or decreased.

It is contemplated that the membrane 11 of this invention may be used in any other design of dispenser for fluid medicaments which is implantable into the human body, as well as in the specific design shown herein. The membrane of this invention may also be used to cover or define any site or area which should be flexible, yet which must be protected from any accidental hypodermic needle penetration. Likewise, the membrane of this invention may be used in any circumstance, in the medical field or elsewhere, where flexibility coupled with strength, and particularly resistance to penetration by a hypodermic needle, is desired. Particularly, the membrane of this invention makes possible the use of an implantable dispenser in which a needle-pierceable fluid resupply port 10 is on the same side of the dispenser as the reservoir membrane 11a. With the membrane, the risk is eliminated of an accidental puncturing of the reservoir by a misdirected needle.

Various variations and modifications can, of course, be made to the preceding description without departing from either the scope or the spirit of the invention.

That which is claimed is:

1. In a body-implantable dispenser for a fluid medicament, the improvement comprising, in combination: a portion of the external wall of said dispenser being defined by a membrane which comprises a fibrous material capable of resisting penetration by a hypodermic needle arranged between a pair of layers of a biocompatible elastomer.

2. The dispenser of claim 1 in which the fibrous material of said membrane is a fabric made of polyaramide fibers.

3. The dispenser of claim 2 in which the opposed, major outer faces of said membrane comprise silicone elastomer.

4. The dispenser of claim 1 in which said biocompatible elastomer layers are made of silicone.

5. The dispenser of claim 1 which includes as a layer of said membrane a water-excluding film.

6. The dispenser of claim 5 in which said water-excluding film is a biaxially oriented polyester material.

7. The dispenser of claim 1 in which said fibrous material is embedded in a bonding resin to secure crossing strands of said fibrous material in immovable relationship.

8. The dispenser of claim 7 in which said resin is an epoxy resin.

9. The body-implantable dispenser of claim 1 in which another portion of the external wall of said dispenser is defined by a resealable, hypodermic needle-penetrable, elastomeric wall having greater ease of needle penetration than said membrane.

10. In a body-implantable dispenser for a fluid medicament, the improvement comprising, in combination: a portion of the external wall of said dispenser comprising a membrane, said membrane comprising at least one layer of a fabric made of polyaramide fibers, the individual fibers of said fabric being bonded together at least their crossing points by a resin, said membrane also comprising a water-excluding film, said membrane defining outer layers of a biocompatible elastomer, whereby said membrane is capable of resisting penetration by a hypodermic needle.

11. The dispenser of claim 10 in which said water-excluding film is biaxially oriented polyester.

12. The dispenser of claim 11 in which the two outer layers of said membrane are silicone elastomer.

13. The dispenser of claim 12 in which said fiber bonding resin is an epoxy resin.

14. The dispenser of claim 13 in which said fabric is woven fabric.

15. The dispenser of claim 14 in which a silicone elastomer layer is positioned between said fabric layer and said water excluding film.

16. In a body-implantable dispenser for a fluid medicament, the improvement comprising, in combination: a portion of the external wall of said dispenser being defined by a membrane which comprises a fibrous material capable of resisting penetration by a hypodermic needle arranged between a pair of layers of biocompatible elastomer, said fibrous material being embedded in a bonding resin to secure crossing strands of said fibrous material in immovable relationship, said membrane also comprising a layer of water-excluding film, in which said water-excluding film layer is separated from said fibrous material by a layer of silicone elastomer.

17. The dispenser of claim 16 in which said biocompatible elastomer layers are made of silicone.

18. The dispenser of claim 17 in which said water excluding film is a biaxially oriented polyester material.

19. The dispenser of claim 18 in which the fibrous material of said membrane is a fabric made of polyaramide fibers.

20. The dispenser of claim 19 in which said bonding resin is an epoxy resin.

* * * * *